United States Patent
Metivier et al.

(10) Patent No.: US 9,976,010 B2
(45) Date of Patent: May 22, 2018

(54) PROCESS FOR THE PRODUCTION OF HYPOPHOSPHITE SALTS

(75) Inventors: Pascal Metivier, Shanghai (CN); Junli Li, Shanghai (CN); Anne Mu, Shanghai (CN)

(73) Assignee: Rhodia Operations, Paris (FR)

( * ) Notice: Subject to any disclaimer, the term of this patent is extended or adjusted under 35 U.S.C. 154(b) by 326 days.

(21) Appl. No.: 14/389,390

(22) PCT Filed: Apr. 6, 2012

(86) PCT No.: PCT/CN2012/073582
§ 371 (c)(1),
(2), (4) Date: Oct. 20, 2014

(87) PCT Pub. No.: WO2013/149396
PCT Pub. Date: Oct. 10, 2013

(65) Prior Publication Data
US 2015/0065626 A1 Mar. 5, 2015

(51) Int. Cl.
*C08K 3/32* (2006.01)
*C01B 25/165* (2006.01)
*C07C 211/63* (2006.01)
*C08K 5/19* (2006.01)

(52) U.S. Cl.
CPC ............. *C08K 3/32* (2013.01); *C01B 25/165* (2013.01); *C07C 211/63* (2013.01); *C08K 5/19* (2013.01); *C08K 2003/329* (2013.01)

(58) Field of Classification Search
CPC .................................. C08K 3/32; C01B 25/165
See application file for complete search history.

(56) References Cited

U.S. PATENT DOCUMENTS

| 3,888,971 | A | 6/1975 | Scheibitz et al. |
| 4,265,866 | A | 5/1981 | Arzoumanidis et al. |
| 5,225,052 | A * | 7/1993 | Takikawa ............ C01B 25/165 |
| | | | 205/488 |
| 2007/0082995 | A1 | 4/2007 | Costanzi et al. |
| 2013/0165564 | A1* | 6/2013 | Zilberman ............ C07F 9/4006 |
| | | | 524/130 |

FOREIGN PATENT DOCUMENTS

| CN | 1056851 A | 12/1991 |
| CN | 1878829 A | 12/2006 |
| CN | 101332982 A | 12/2008 |
| WO | 2005/044906 A1 | 5/2005 |
| WO | 2011/047511 A1 | 4/2011 |

* cited by examiner

*Primary Examiner* — Arrie L Reuther

(57) ABSTRACT

Disclosed is a process to produce a hypophosphite salt defined as [$C^+$ hypophosphite$^-$] by reacting $P_4$ with a hydroxide salt defined as [$C^+OH^-$], or a hydroxide salt precursor and a catalyst, wherein $C^+$ is the cationic moiety of [$C^+$ hypophosphite$^-$] salt.

15 Claims, No Drawings

PROCESS FOR THE PRODUCTION OF HYPOPHOSPHITE SALTS

CROSS-REFERENCE TO RELATED APPLICATIONS

The present application is a U.S. national stage entry under 35 U.S.C. § 371 of International Application No. PCT/CN2012/073582 filed Apr. 6, 2012, the whole content of this application being herein incorporated by reference for all purposes.

The present invention concerns a process for the production of a hypophosphite salt using at least P4 and a catalyst. Base that can be used is preferably a hydroxide salt or a hydroxide salt precursor that can also be used as catalyst of the instant invention.

PRIOR ART

The hypophosphite salts and, especially, calcium hypophosphite, can be prepared for example from white phosphorus ($P_4$) reacted under alkaline conditions with calcium hydroxide or calcium oxide and water as taught by U.S. Pat. No. 5,225,052. It is also possible to obtain calcium hypophosphite by reaction of a calcium salt or simply from lime as taught by Chinese patent CN101332982, with hypophosphorous acid. For example the lime suspension is simply neutralized with hypophosphorous acid, the Impurities are removed by filtration and the product isolated in a same way as previously described. It is also possible to obtain calcium hypophosphite from other metallic hypophosphites or the acid by ion exchange process.

DEFINITION OF THE INVENTION

In a first embodiment the present invention concerns a process for the production of a hypophosphite salt using at least P4 and a catalyst. The present invention then concerns a process to produce a hypophosphite salt defined as [$C^+$ Hypophosphite$^-$] by reacting P4 with a hydroxide salt, defined as [$C^+OH^-$], or a hydroxide salt precursor, and a catalyst; wherein $C^+$ is the cationic moiety of [$C^+$ Hypophosphite$^-$] salt.

The reaction of the Instant invention may be established as follows:

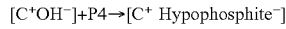

[$C^+OH^-$]+P4→[$C^+$ Hypophosphite$^-$]

This process permits then to produce hypophosphite salts, but also phosphate salts as a by product. Such a process according to the present invention permits to obtain a molar ratio of hypophosphite salt/phosphite salt superior to 1.5; preferably superior or equal to 1.6, more preferably superior or equal to 1.7, notably superior or equal to 2.0; permitting thereof to increase the selectivity of the reaction.

The invention also concerns a blend of hypophosphite salts and phosphate salts susceptible to be obtained by the process of the present invention.

According to the generic definition, salts are ionic compounds that result from the neutralization reaction of an acid and a base. There are composed of cations that are positively charged ions and anions that are negative ions; so that the product is electrically neutral.

$P_4$ is the tetraphosphorus, also called "white phosphorus", consisting of six single P—P bonds.

Catalyst as defined in the invention is a substance changing the rate of the reaction of the invention without being consumed by the reaction itself, contrarily to the other reagents.

In a preferred embodiment of the present invention, catalysts are preferably quaternary ammonium salts or phosphonium salts.

More preferably the quaternary ammonium salt catalyst of the present invention is a quaternary ammonium salt of formula (I)

(I)

wherein:
$R^1$, $R^2$, $R^3$ and $R^4$ independently of one another represent an organic hydrocarbon group, and
X is an organic or an Inorganic anion.

$R^1$, $R^2$, $R^3$ and $R^4$ independently of one another preferably represent a branched or unbranched alkyl group having 1-18 carbon atoms, more preferably having 1-6 carbon atoms. $R^1$, $R^2$, $R^3$ and $R^4$ independently of one another can also represent an aryl, alkylaryl or arylalkyl group having 6-18 carbon atoms, more preferably having 6-10 carbon atoms. Said organic hydrocarbon group may be branched or unbranched, saturated or unsaturated. Said group can notably be an aliphatic or an aromatic group.

In a preferred embodiment, $R^1$, $R^2$, $R^3$ and $R^4$ independently of one another preferably represent an alkyl group having 1-6 carbon atoms, such as methyl, ethyl, propyl, and butyl.

As previously defined, X is an organic or an inorganic anion that may be OH, a halogen atom, a sulfate, a carbonate or an alkylate. Halogen atom may be for example F, Cl, Br or I. Alkylate anions may be for example acetate. X is preferably an OH or a halogen such as Cl or Br.

Compounds of formula (I) are preferably chosen in the group consisting of: tetrabutylammonium hydroxide, tetrabutylammonium chloride, tetrabutylammonium bromide, benzalkonium chloride, tetraethylammonium hydroxide, tetramethylammonium chloride, tetramethylammonium hydroxide, tetraethylammonium bromide, cetrimonium bromide, dimethyldioctadecylammonium chloride, benzyltrimethylammonium chloride, benzyltrimethylammonium bromide, tetrabutylammonium acetate, and tetrapropylammonium hydroxide.

Preferred molar proportions of catalyst may be comprised between 0.1 and 40%, in relation with the mol of P4. Preferred molar proportions of catalyst may be comprised between 0.1 and 40%, in relation with the mol of [$C^+OH^-$]. Preferred molar proportions of quaternary ammonium salt are comprised between 10 and 40%, in relation with the mol of P4.

$C^+$ is the cationic moiety of [$C^+$ Hypophosphite$^-$] salt; that may represent an inorganic element such as a metal, an alkali earth metal, an alkali metal or a quaternary ammonium salt or quaternary phosphonium salt. $C^+$ is preferably an alkali earth metal, such as Ca or Mg, or an alkali metal, such as Li, Na or K, a quaternary ammonium salt or quaternary phosphonium salt.

As previously defined, a hydroxide salt precursor of [$C^+OH^-$] may be used in the process of the invention. Such hydroxide salt precursor can be for example an oxide precursor, such as calcium oxide permitting to obtain calcium hydroxide, in presence of water.

It has to be noticed that [C$^+$OH$^-$] may be the catalyst used in the reaction, such as for example the quaternary ammonium salt as catalyst of formula (I).

The preferred molar ratio [C$^+$OH$^-$]/P4 is comprised between 0.5 and 4, more preferably between 1.0 and 2.0.

The hypophosphite salt present in the composition according to the invention is preferably a compound of the formula (II) as defined below:

wherein:
- n is comprised between 1 and 5, more preferably 1, 2 or 3; and
- C is a cation, preferably an alkali earth metal, such as Ca or Mg, or an alkali metal, such as Li, Na or K, a quaternary ammonium salt or quaternary phosphonium salt.

The hypophosphite salt is more preferably chosen in the group consisting of: sodium hypophosphite, tetrabutylammonium hypophosphite, tetramethylammonium hypophosphite, tetramethylammonium hypophosphite, calcium hypophosphite, aluminium hypophosphite, lanthanum hypophosphite, and cesium hypophosphite.

Reaction of the present invention can occur at a temperature comprised between 50 and 150° C., preferably comprised between 80 and 120° C. Pressure during the reaction may be between 0.5 and 1.5 bar as example.

Process of the present invention may be carried out without or with a solvent. Preferred solvents are polar solvent such as water or alcohols.

pH of the reaction is generally alkaline, that is superior to 7; notably comprised between 7.1 and 14.

The quality of the hypophosphite salts may be determined by detecting the remaining impurities using thermal analysis tools such as ARC (Adiabatic Reaction Calorimeter) and TGA (Thermal Gravimetric Analysis).

At the end of the reaction, it's perfectly possible to remove some impurities or by-products by several ways of purification methods, such as for example filtration, centrifugation, extraction, crystallization, distillation or fractionation. It is notably possible to remove phosphate salts by filtration then crystallization.

Reaction of the present invention may be carried out in a continuous, semi-continuous or discontinuous way. Said reaction may be made as example in a stirring reactor, a stirring reactor with a condenser, a tubular reactor, or a plug flow reactor.

It has to be noticed that addition of base hydroxide salt, defined as [C$^+$OH$^-$], can be batch or continuous.

The hypophosphite salt as produced in the present invention may be further stabilized, notably for its use in the field of plastic. A process for stabilizing said hypophosphite salt, may comprise the steps of:
- a) washing the starting hypophosphite salt at least one time, preferably 2 or 3 times, under a controlled value of pH comprised between 4 and 11, preferably between 5 and 8, said hypophosphite salt being in an aqueous solution and/or in a solid state, and eventually washing at least one time the hypophosphite salt with an organic solvent miscible with water, and
- b) drying the hypophosphite salt as obtained after the washing operation(s) of step (a) under reduced pressure to remove the volatiles.

According to a first possible embodiment, the starting hypophosphite salt which is used in step a) can be in the form of an aqueous solution, charged in a reactor and mixed with a mineral or an organic acid to obtain a slurry whose pH is set at a value of between 4 and 6.5, preferably 5 and 6. The acid used in this connection is preferably selected from the group comprising hypophosphorous acid, citric acid, maleic acid, acetic acid, chlorhydric acid and sulphuric acid and, more preferably, the acid is hypophosphorous acid.

According to another embodiment, the starting hypophosphite salt of step a) may alternatively be in the form of an aqueous solution, charged in a reactor and mixed with a mineral or an organic base to obtain a slurry whose pH is set at a value of between 7.5 and 11, preferably 8 and 10. In that case the base is preferably selected from the group comprising sodium hydroxide, potassium hydroxide, calcium hydroxide, calcium oxide, magnesium oxide and magnesium hydroxide, even more preferably, the base is calcium hydroxide and/or calcium oxide.

The process for stabilizing the hypophosphite salt can be batch, continuous or semi-continuous and be performed in a close or open system under inert atmosphere. That inert atmosphere can be for example carbon dioxide, argon, or nitrogen. The process for stabilizing the hypophosphite salt can be performed under atmospheric pressure, under pressure or under vacuum.

A way to check the quality of the heat stabilized hypophosphite salt used in the instant invention, is to perform a stability test at elevated temperature on the product, alone or mixed with plastic and measure the amount of phosphine generated during the test. It is also possible to measure the amount of phosphine generated when the product is compounded with plastics such as polyamide.

Hypophosphite salt produced according to the present invention may notably be used as flame retardant agent in polymer compositions, preferably in thermoplastic polymer compositions. The invention then also concerns a thermoplastic composition comprising at least a hypophosphite salt as produced with the process as described.

Typically, the polymer present in a flame retardant polymer composition of the invention is selected from the group consisting in polyphenylene ethers, polyamides, polyesters, polycarbonates, epoxy resins, phenolic resins, acrylonitrile butadiene styrene (ABS), styrene acrilonitrile (SAN), polystyrene such as high impact polystyrene (HIPS), polyphenylene ethers such as PPO, styrene butadiene rubber (SBR), halogenated polymers such as polyvinylchloride (PVC), and mixtures and blends of these polymers. Polyamides are preferably PA66, PA6, PA11, PA12, PA6.10, high temperature polyamides such as PPA, PA4.6, PA9T, PA66.6T, PA10T, PA6.6T and blends of polyamides, such as PA/PET, PA/ABS or PA/PP. Polyesters may be polyethylene terephthalate (PET) or polybutylene terephthalate (PBT).

The following examples are included to illustrate embodiments of the invention. It should be appreciated by those of skill in the art that the techniques disclosed in the examples that follow represent techniques discovered by the inventor to function well in the practice of the invention.

EXPERIMENTAL PART

Example 1: Bu$_4$NOH as Catalyst

Equimolar proportions of P$_4$, Ca(OH)$_2$ and H$_2$O are reacted with different loading of Bu$_4$NOH (% mol in relation with mol of the P$_4$).

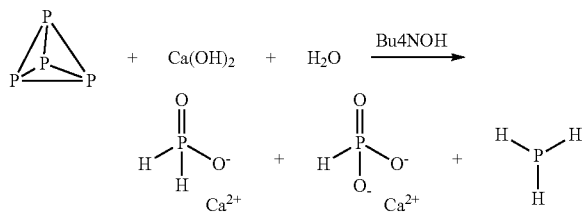
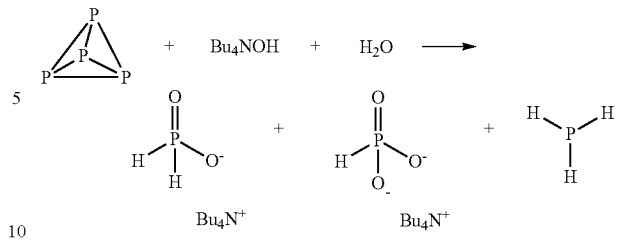

A flask was equipped with cooling condenser and magnetic stir under a flow of argon and the out gas was collected by a gas bag. Under argon protection, this flask was charged with 1.52 g (0.049 mol) P4 and 1.93 g H$_2$O. Then 4.92 g (0.066 mol) Ca(OH)$_2$ and 19.12 g (0.007 mol) Bu$_4$NOH (10% water solution) were added into and the resulting mixture was heated to 95° C. for 4 h with generated phosphine collection by gas bag. When reaction was completed, reaction mixture was cooled down. After using concentrated HCl to dissolve all solid, 0.4 g H$_3$PO$_4$ (85%) was added as internal standard of P-NMR. P-NMR analysis showed this mixture contained 33.9% hypophosphite and 19.2% phosphate with ratio of 1.8

P-NMR (300 MHz, D$_2$O, decoupling): δ 11.98 (hypophosphite), 4.52 (phosphite), −0.414 (phosphate)

A flask was equipped with cooling condenser and magnetic stir under a flow of argon and the out gas was collected by a gas bag. Under argon protection, this flask was charged with 1.52 g (0.049 mol) P4 and 3.82 g H$_2$O. Then 4.31 g (0.058 mol) Ca(OH)$_2$ and 37.7 g (0.015 mol) Bu$_4$NOH (10% water solution) were added into and the resulting mixture was heated to 95° C. for 4 h with generated phosphine collection by gas bag. When reaction was completed, reaction mixture was cooled down. After using concentrated HCl to dissolve all solid, 0.4 g H$_3$PO$_4$ (85%) was added as internal standard of P-NMR. P-NMR analysis showed this mixture contained 38.4% hypophosphite and 18.5% phosphate with ratio of 2.1

P-NMR (300 MHz, D$_2$O, decoupling): δ 11.98 (hypophosphite), 4.52 (phosphite), −0.414 (phosphate)

Results are expressed in Table 1

TABLE 1

| Catalyst (mol %) | Hyphosphite/Phoshite ratio |
| --- | --- |
| 0 | 1.5 |
| 15 | 1.8 |
| 30 | 2.0 |

It appears then that the use of a catalyst in the reaction permits to increase the Hyphosphite/Phoshite ratio.

Example 2: Bu$_4$NOH as Catalyst and as Reactant

Some proportions of P$_4$, Bu$_4$NOH and H$_2$O are reacted with Bu$_4$NOH as catalyst A flask was equipped with cooling condenser and magnetic stir under a flow of argon and the out gas was collected by a gas bag. Under argon protection, this flask was charged with 0.15 g (0.005 mol) P4 and 42.9 g H2O. Then 1.88 g (0.007 mol) Bu$_4$NOH (10% water solution) was added into and the resulting mixture was heated to 95° C. for 4 h with generated phosphine collection by gas bag. When reaction was completed, reaction mixture was cooled down. After using concentrated HCl to dissolve all solid, 0.4 g H$_3$PO$_4$ (85%) was added as internal standard of P-NMR. P-NMR analysis showed this mixture contained 43.5% hypophosphite and 18.9% phosphate with ratio of 2.3

P-NMR (300 MHz, D$_2$O, decoupling): δ 11.98 (hypophosphite), 4.52 (phosphite), −0.414 (phosphate)

A flask was equipped with cooling condenser and magnetic stir under a flow of argon and the out gas was collected by a gas bag. Under argon protection, this flask was charged with 0.66 g (0.021 mol) P4 and 30.4 g H2O. Then 3.38 g (0.013 mol) Bu$_4$NOH (10% water solution) was added into and the resulting mixture was heated to 95° C. for 4 h with generated phosphine collection by gas bag. When reaction was completed, reaction mixture was cooled down. After using concentrated HCl to dissolve all solid, 0.4 g H$_3$PO$_4$ (85%) was added as internal standard of P-NMR. P-NMR analysis showed this mixture contained 22.6% hypophosphite and 9.3% phosphate with ratio of 2.43

P-NMR (300 MHz, D$_2$O, decoupling): δ 11.98 (hypophosphite), 4.52 (phosphite), −0.414 (phosphate)

A flask was equipped with cooling condenser and magnetic stir under a flow of argon and the out gas was collected by a gas bag. Under argon protection, this flask was charged with 0.38 g (0.012 mol) P4 and 9.43 g H$_2$O. Then 4.9 g (0.019 mol) Bu$_4$NOH (10% water solution) was added into and the resulting mixture was heated to 95° C. for 4 h with generated phosphine collection by gas bag. When reaction was completed, reaction mixture was cooled down. After using concentrated HCl to dissolve all solid, 0.4 g H$_3$PO$_4$ (85%) was added as internal standard of P-NMR.

P-NMR analysis showed this mixture contained 34.1% hypophosphite and 11.8% phosphate with ratio of 2.89

P-NMR (300 MHz, D$_2$O, decoupling): δ 11.98 (hypophosphite), 4.52 (phosphite), −0.414 (phosphate)

Results are expressed in Table 2.

TABLE 2

| P4 (mol) | Bu$_4$NOH (mol) | H$_2$O (mol) | Bu$_4$NOH/P$_4$ | Bu$_4$NOH/H$_2$O | Hypophophite (%) | Conversion | Hyphosphite/Phoshite Ratio |
| --- | --- | --- | --- | --- | --- | --- | --- |
| 0.005 | 0.007 | 2.381 | 1.400 | 0.003 | 43.5 | 62.4 | 2.30 |
| 0.021 | 0.013 | 1.688 | 0.619 | 0.008 | 22.6 | 31.9 | 2.43 |
| 0.012 | 0.019 | 0.523 | 1.583 | 0.036 | 34.1 | 45.9 | 2.89 |

It appears then that the use of a compound as a hydroxide salt and a catalyst in the reaction permits to increase the Hyphosphite/Phoshite ratio.

What is claimed is:

1. A process to produce a hypophosphite salt defined as [$C^+$ Hypophosphite$^-$] by reacting $P_4$ with a hydroxide salt, defined as [$C^+OH^-$], or a hydroxide salt precursor; and a quaternary ammonium salt or a phosphonium salt; wherein $C^+$ is the cationic moiety of [$C^+$ Hypophosphite$^-$] salt.

2. The process according to claim 1, wherein said process permits to the production of a hypophosphite salt and a phosphite salt with a molar ratio of said hypophosphite salt/said phosphite salt greater than 1.5.

3. The process according to claim 1, wherein the quaternary ammonium salt is a quaternary ammonium salt of formula (I):

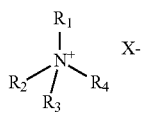
(I)

wherein:
$R^1$, $R^2$, $R^3$ and $R^4$ independently of one another represent an organic hydrocarbon group, and
X is an organic or an inorganic anion.

4. The process according to claim 3, wherein $R^1$, $R^2$, $R^3$ and $R^4$ independently of one another represent a branched or unbranched alkyl group having 1-18 carbon atoms.

5. The process according to claim 3, wherein X is an organic or an inorganic anion that is OH, a halogen atom, a sulfate, a carbonate or an alkylate.

6. The process according to claim 3, wherein compounds of formula (I) are selected from the group consisting of tetrabutylammonium hydroxide, tetrabutylammonium chroride, tetrabutylammonium bromide, benzalkonium chloride, tetraethylammonium hydroxide, tetramethylammonium chloride, tetramethylammonium hydroxide, tetraethylammonium bromide, cetrimonium bromide, dimethyldioctadecylammonium chloride, benzyltrimethylammonium chloride, benzyltrimethylammonium bromide, tetrabutylammonium acetate, and tetrapropylammonium hydroxide.

7. The process according to claim 1, wherein the molar proportions of quaternary ammonium salt or a phosphonium salt is between 0.1 and 40%, in relation with the mol of $P_4$.

8. The process according to claim 1, wherein the molar proportions of quaternary ammonium salt is between 10 and 40%, in relation with the mol of $P_4$.

9. The process according to claim 1, wherein $C^+$ is the cationic moiety of [$C^+$ Hypophosphite$^-$] salt that represents a metal, an alkali earth metal, an alkali metal or a quaternary ammonium or quaternary phosphonium.

10. The process according to claim 1, wherein said [$C^+OH^-$] is a quaternary ammonium salt or a phosphonium salt.

11. The process according to claim 10 wherein [$C^+OH^-$] is a quaternary ammonium salt of formula (I):

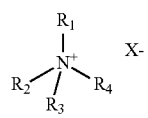
(I)

wherein:
$R^1$, $R^2$, $R^3$ and $R^4$ independently of one another represent an organic hydrocarbon group, and
X is OH$^-$.

12. The process according to claim 1, wherein the molar ratio [$C^+OH^-$]/$P_4$ is comprised between 0.5 and 4.

13. The process according to claim 1, wherein the hypophosphite salt is a compound of the formula (II) as defined below:

$$[H_2\text{-}P(=O)\text{---}O^-]_n C^{n+} \quad (II)$$

wherein:
n is comprised between 1 and 5; and
C is a cation.

14. The process according to claim 1, wherein said reaction occurs at a temperature between 50 and 150° C.

15. The process according to claim 1, wherein said pH of the reaction is greater than 7.

* * * * *